United States Patent [19]

Usami et al.

[11] Patent Number: 4,851,103
[45] Date of Patent: Jul. 25, 1989

[54] MOISTURE MEASURING DEVICE FOR HIGH TEMPERATURE GAS

[75] Inventors: Jun Usami, Nukata; Toru Kodachi, Nagoya, both of Japan

[73] Assignee: NGK Insulators, Ltd., Nagoya, Japan

[21] Appl. No.: 100,457

[22] Filed: Sep. 24, 1987

[30] Foreign Application Priority Data

Sep. 30, 1986 [JP] Japan ................................ 61-230128

[51] Int. Cl.$^4$ ............................................ G01N 27/58
[52] U.S. Cl. .................... 204/406; 204/1 T; 204/410; 204/412; 204/425
[58] Field of Search .............. 204/425, 412, 1 W, 1 S, 204/406, 410

[56] References Cited

U.S. PATENT DOCUMENTS 4,264,425  4/1981  Kimura et al. .................. 204/425 X
4,576,705  3/1986  Kondo et al. ........................ 204/406

Primary Examiner—G. L. Kaplan
Attorney, Agent, or Firm—Arnold, White & Durkee

[57] ABSTRACT

A moisture ($H_2O$) measuring device for high temperature gas deriving the moisture content by taking a difference between measured values of oxygen concentration by an operational process. The one value of the an oxygen concentration is for oxygen content originally included in the measuring gas and the other value of the oxygen concentration is one additionally including oxygen content obtained by electrolysis of the moisture in the measuring gas. The two measured values are controlled by applying voltage for the oxygen pump.

3 Claims, 8 Drawing Sheets

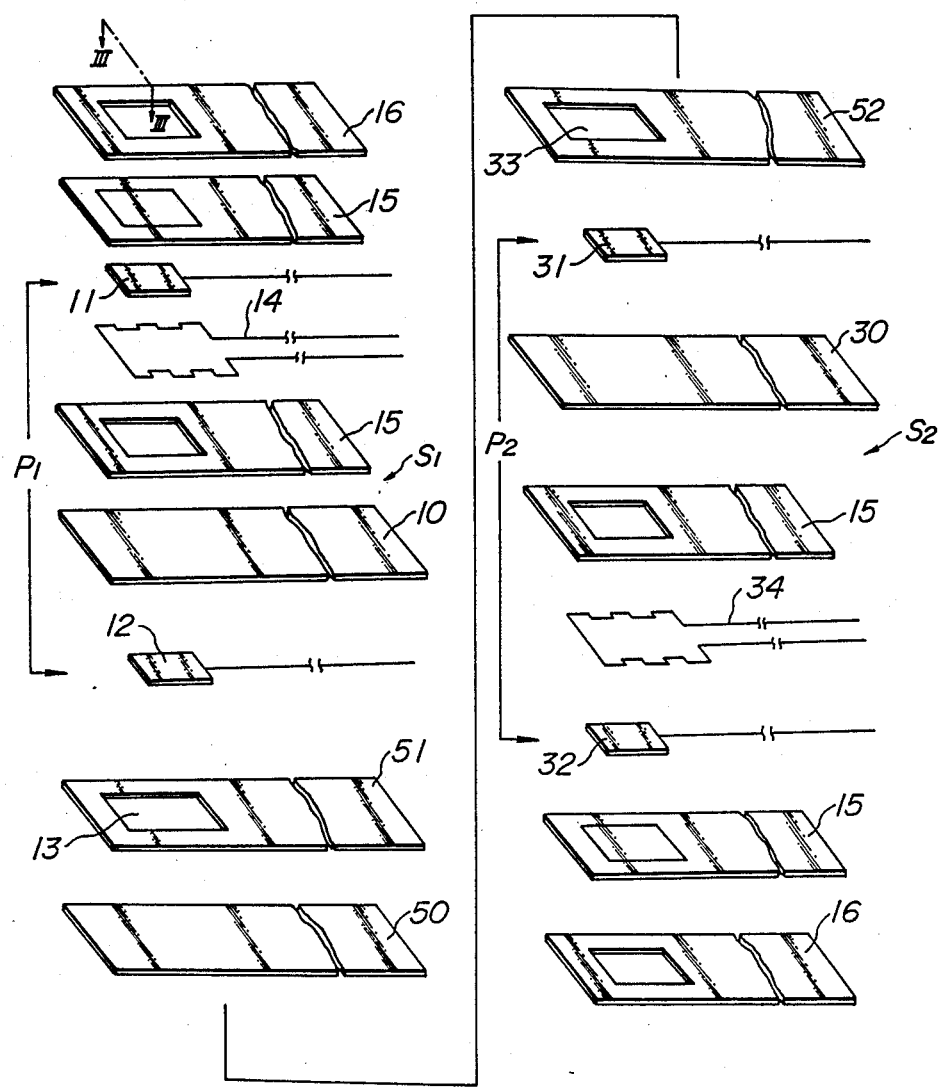
FIG_1

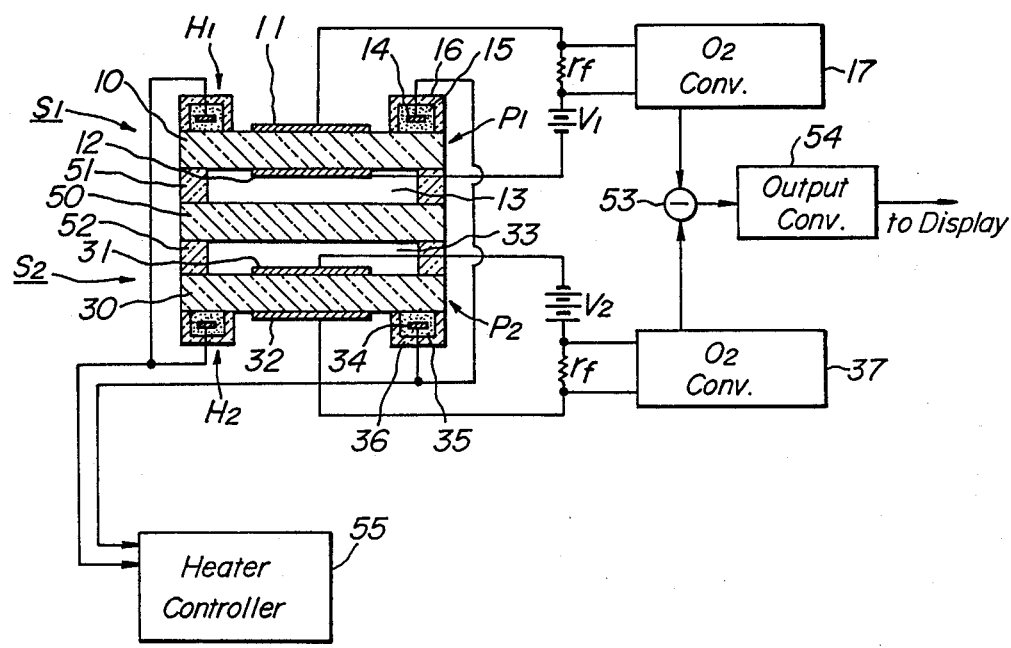
FIG_2

FIG_3
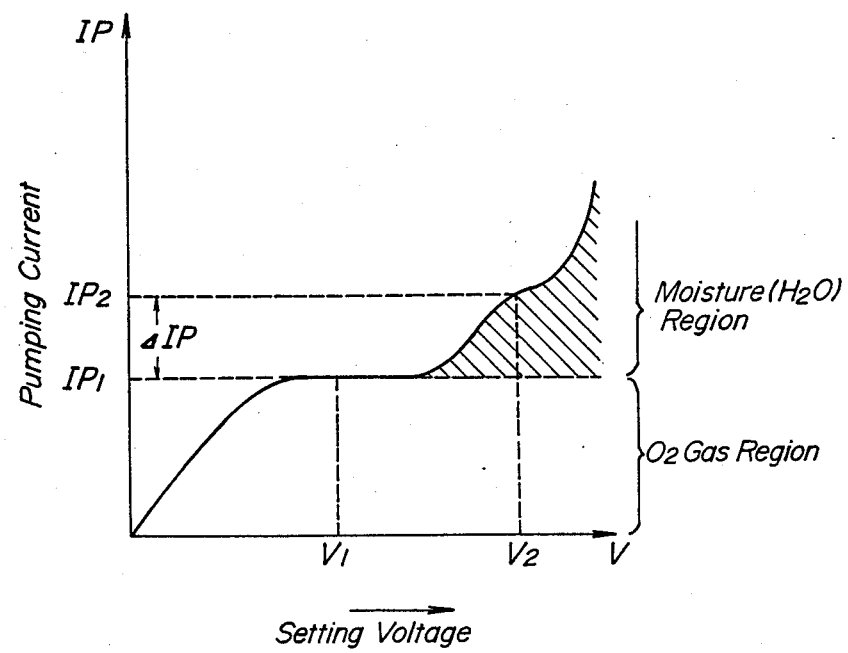

FIG_4
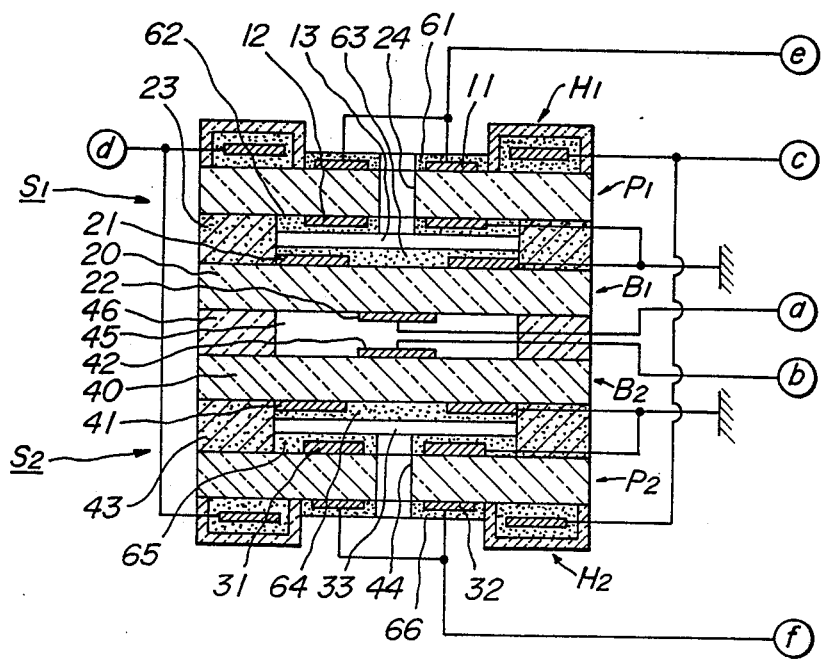

FIG_5
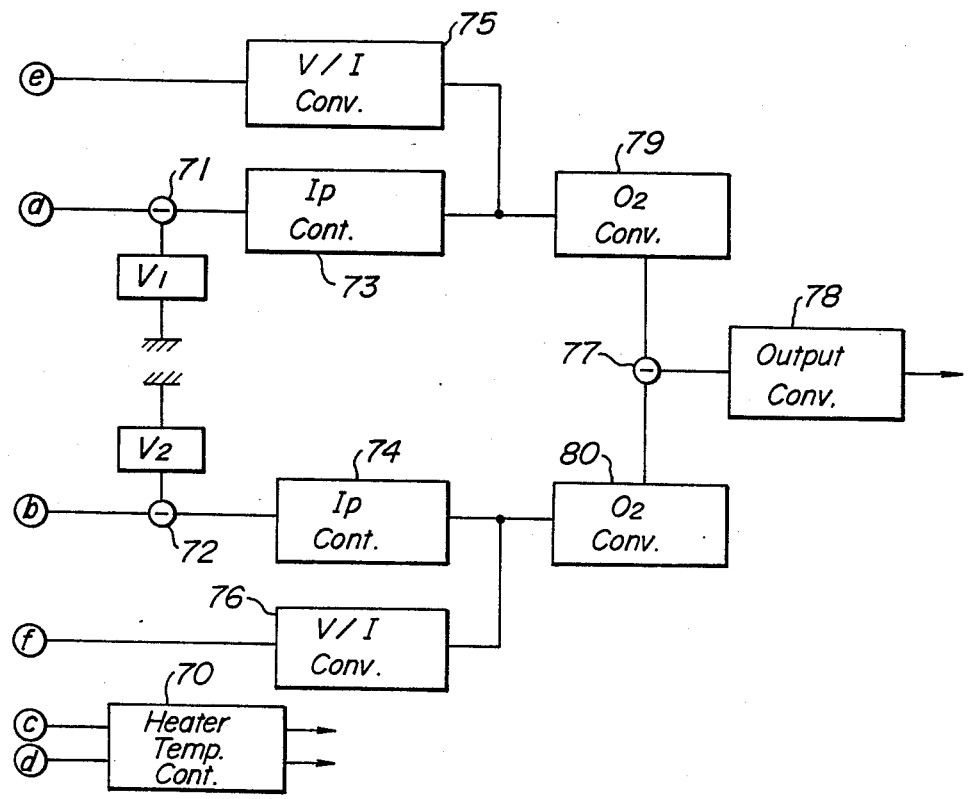

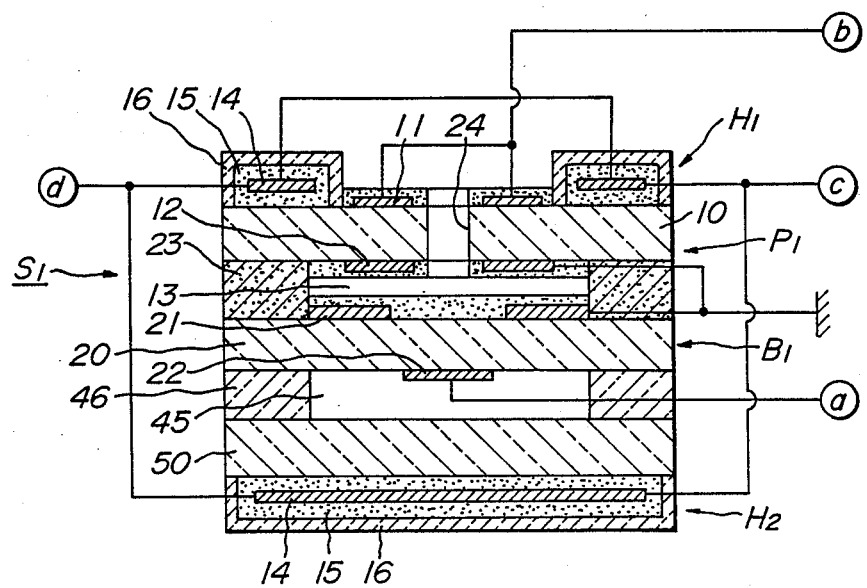
FIG_6

MOISTURE MEASURING DEVICE FOR HIGH TEMPERATURE GAS

BACKGROUND OF THE INVENTION

1. Field of the Invention

The present invention relates to a moisture measuring device for measuring a moisture ($H_2O$) concentration in a measuring gas by taking a difference between an oxygen concentration based solely on the oxygen partial pressure in the measuring gas and an oxygen concentration including the oxygen partial pressure obtained by an electrolysis of the moisture ($H_2O$) in the measuring gas.

2. Related Art Statement

Moisture measuring devices for measuring moisture concentration or water content in a measuring gas consisting of a base gas including oxygen and vaporized water by using an oxygen concentration detecting device formed of a solid electrolyte member are known, for instance, from that disclosed in Japanese patent application laid opened number 60-105,957. This moisture measuring device disclosed in the abovementioned patent specification comprises a gas storing chamber provided with a small hole for introducing the measuring gas including moisture and oxygen, a solid electrolyte type oxygen concentration detector so arranged in the gas storing chamber that the measuring electrodes come in contact with the measuring gas introduced in the gas storing chamber, and a standard gas supplying mechanism which removes the measuring gas from the gas storing chamber and supplies the measuring gas to a comparing electrode portion of the oxygen concentration detector. The standard gas supplying mechanism comprises a standard gas extracting tube, a dehumidifier for removing moisture from the measuring gas taken out by the extracting tube, and a pump for transporting the measuring gas through the extracting tube. The dehumidifier is connected directly to the gas outlet of the gas extracting tube or connected to the gas outlet through a coupling tube heated by a heater or the like and the moisture concentration or water content in the measuring gas is measured by using an oxygen concentration detector.

In such a known moisture measuring device, however, as the measuring gas is once introduced into a dehumidifier outside a furnace by a pump and a reference gas is obtained, the construction of the device inevitably becomes complicated and bulky. Furthermore, essentially there is unavoidable measuring error based on the time difference between the measuring gas directly introduced to the location of the measuring electrodes and the dehumidified gas introduced into the location of comparing electrodes in the oxygen concentration detector after dehumidification. This measuring error can not be removed even suppressing the variation of the oxygen concentration by taking the average of the variation. Also as the measuring gas is dried in the dehumidifier, the response time of the overall system becomes longer at least by the time required for the drying.

SUMMARY OF THE INVENTION

The present invention has for its object to realize a moisture measuring device having a small shape and having a good response characteristic without using the dehumidifier or the like.

The moisture measuring device according to the present invention is characterized in that the device comprises a sensor element including an oxygen pump, a controlling circuit for controlling said sensor element, an operational circuit for processing signals obtained from said sensor element, wherein the controlling circuit applies to said oxygen pump a first setting voltage which does not electrolytically decompose the moisture content in the measuring gas and a second setting voltage which does electrolytically decompose the moisture content in the measuring gas, respectively. The operational circuit derives the moisture concentration in the measuring gas by obtaining a difference between respective currents flowing through the oxygen pumps caused by said voltages by an operational processing.

A preferred embodiment of the present invention is characterized in that the device comprises two sensor elements arranged in symmetry with flow of the measuring gas, and said controlling circuit supplies the first and the second setting voltages to the oxygen pumps of the two sensor elements respectively, and the moisture concentration in the measuring gas is derived by obtaining a difference between the respective currents flowing through the two oxygen pumps.

The device according to the present invention having the abovementioned construction has its feature in that the two oxygen pumps are allotted with two separate functions by setting the respective applying voltages to predetermined values. Stated differently one oxygen pump is to detect only the oxygen content originally contained in the measuring gas including moisture content and another oxygen pump is to detect not only the oxygen content originally contained in the measuring gas but also the oxygen content obtained by electrolysis of the moisture ($H_2O$) content in the measuring gas, and by taking a difference between the pumping currents flowing through the oxygen pumps and a current value corresponding to the oxygen concentration obtained only by the electrolysis of the moisture content is derived by an operational circuit. The oxygen concentration obtained from this current value is in proportion to the amount of moisture content in the measuring gas so that the moisture content is measured from the amount of the above oxygen concentration.

BRIEF DESCRIPTION OF THE DRAWINGS

FIG. 1 is an exploded view of sensor element used in the moisture measuring device according to the present invention;

FIG. 2 is a cross-sectional view of the sensor element;

FIG. 3 is a diagram for showing the principle of the moisture measurement;

FIGS. 4 and 5 show a second embodiment of the present invention in cross-sectional view and block diagram;

FIGS. 6, 7A and 7B show a third embodiment of the present invention in cross-sectional view, block diagram and the timing chart thereof.

DETAILED DESCRIPTION OF THE PREFERRED EMBODIMENTS

Figure 7A:
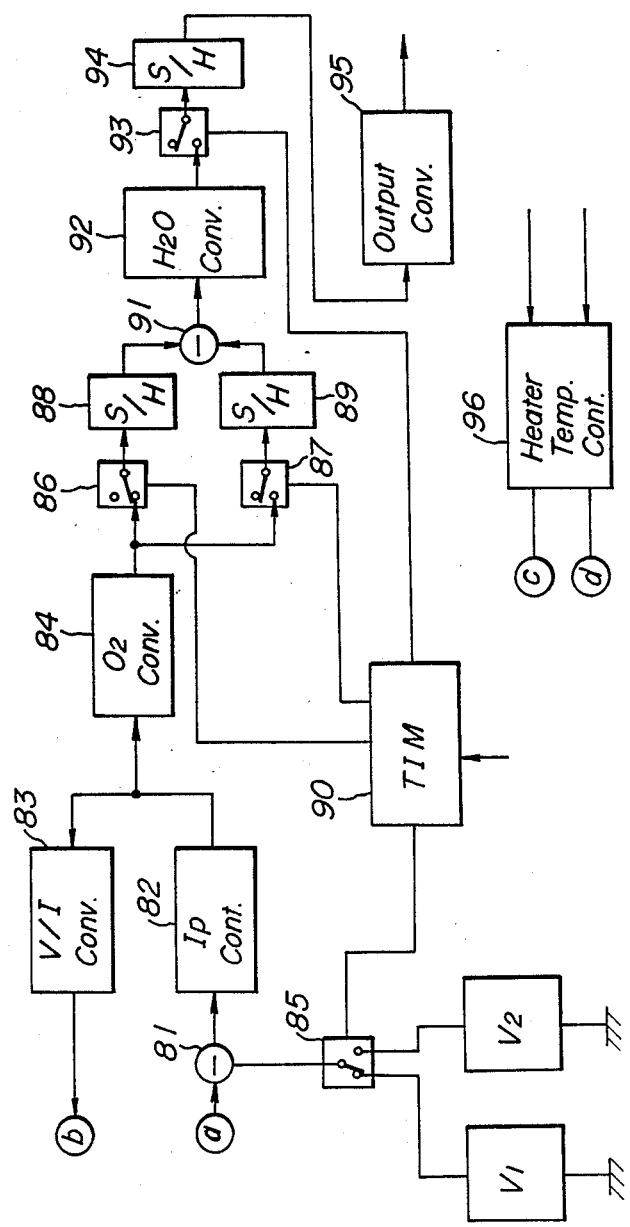

In order to clearly explain the concept of the present invention, several preferred embodiments of the present invention will now be described in detail by referring to the accompanying drawings.

FIGS. 1 and 2 show one embodiment of the sensor element of the moisture measuring device according to the present invention in exploded perspective view and cross-sectional view.

At the upper side or top of this sensor element, a first oxygen pumping portion $P_1$ comprising a solid electrolyte member 10 and upper and lower pumping electrodes 11 and 12 arranged at upper and lower sides of the solid electrolyte member 10 is provided. An upper heater portion $H_1$ as shown in FIG. 2 may be provided over the top surface of the oxygen pumping portion $P_1$ to surround the upper pumping electrode 11. The abovementioned elements form sensor element $S_1$.

Then, at the lower side or bottom of the device, a second oxygen pumping portion $P_2$ comprising a solid electrolyte member 30 and upper and lower pumping electrodes 31 and 32 arranged at upper and lower sides of the solid electrolyte member 30 is provided. As with $P_1$, a lower heater portion $H_2$ as shown in FIG. 2 may be provided at the bottom surface of the oxygen pumping portion $P_2$ to surround the lower pumping electrode 32. The abovementioned elements form the sensor element $S_2$.

An additional solid electrolyte member 50 is provided between the two pumping portions $P_1$ and $P_2$. Also porous spacer members 51 and 52 made from alumina or the like are interposed between the solid electrolyte member 50 and the upper and lower solid electrolyte members 10 and 30, respectively, as the diffusion resistance means. The measuring gas is introduced into a diffusion chamber 13 formed as a very narrow gap flat space surrounded by the spacer member 51 and the solid electrolyte members 10 and 50 and also into a diffusion chamber 33 likewisely formed as a very narrow gap flat space surrounded by the spacer member 52 and the solid electrolyte members 50 and 30 through the respective spacer members 51 and 52 with a certain diffusion resistance. The measuring gas comes in contact with the pumping electrodes 12 and 32 in the respective diffusion chambers 13 and 33.

The solid electrolyte members 10, 30 and 50 are made of stabilized or partially stabilized zirconia ceramics which show oxygen ion conductivity at high temperatures. As is known in the art, the stabilized or partially stabilized zirconia ceramics may be obtained by forming a solid solution of zirconium oxide with yttrium oxide, calcium oxide, and the like etc. Each of the electrodes 11, 12, 31 and 32 is formed of porous platinum or the like.

Heater elements 14 and 34 of the heater portions $H_1$ and $H_2$ are covered by porous layers 15 and 35, respectively, formed of alumina or the like, having electrical insulating properties. Over these porous layers 15 and 35, air tight layers 16 and 36 are provided respectively formed of solid electrolyte, such as zirconia or the like. The heater elements 14 and 34 are separated or isolated from the outer measuring gas in the construction mentioned above. The heater elements 14 and 34 may be formed, for instance, by printing using paste having as the main constituents of alumina powder and platinum powder or by arranging a cermet like film on a base.

The respective oxygen pumping portions $P_1$ and $P_2$ of the sensor elements $S_1$ and $S_2$ arranged symmetrically with each other and the heater portions $H_1$ and $H_2$ thereof are laminated as shown in FIG. 2 to form an integrated narrow width elongated plate shape body and sintered to form a unit member.

The sensor element having the integrated and laminated construction is connected with a controlling circuit and an operational circuit. The function of these circuits and the sensor element will be explained hereinafter by referring to FIG. 2.

A setting voltage $V_1$ is applied across the pumping electrodes 11 and 12 of the sensor elements $S_1$ through a series connected standard resistance $r_f$. At both terminals of the standard resistance $r_f$, two input terminals of an oxygen ($O_2$) converter 17 are connected. Output terminals of the oxygen converter 17 are connected to one input terminal of a subtractor 53. Output terminals of the subtractor 53 are connected to an input terminal of an output converter 54 of which an output terminal thereof is connected to a display device provided outside of the device.

Likewisely, a setting voltage $V_2$ is applied across the pumping electrodes 31 and 32 of the sensor element $S_2$ through a series connected standard resistance $r_f$. At both terminals of the standard resistance $r_f$, input terminals of an oxygen ($O_2$) converter 37 are connected. An output terminal of this oxygen converter 37 is connected to the other input terminal of the subtracter 53.

A heater controller 55 connected to a heater current source (not shown) is connected to the current supply terminals of the heater elements 14 and 34 of the upper and the lower heater portions $H_1$ and $H_2$.

The moisture measurement by means of the moisture measuring device having the construction as mentioned above will be explained.

The principle of the moisture measurement is to take a difference between the following two conditions. Basically, the measuring gas is assumed to contain moisture, oxygen and nitrogen. Depending upon the voltage to be applied to the electrodes of the oxygen pump, there is a case that only the oxygen gas passes the solid electrolyte member forming the oxygen pump as an oxygen ion and a case that not only the oxygen ion of the originally included oxygen gas but also an oxygen ion being produced by the electrolysis of moisture ($H_2O$) expressed by the following formula;

$$H_2O \rightarrow H_2 + \tfrac{1}{2}O_2$$

may pass the solid electrolyte member forming the oxygen pump. By this reason, the oxygen pumping current Ip may variate as shown in the diagram of FIG. 3.

Namely, if the oxygen pump $P_1$ is driven by a setting voltage $V_1$, which does not act to decompose the moisture ($H_2O$) content by electrolysis and if the oxygen pump $P_2$ is driven by a different setting voltage $V_2$, which acts to decompose the moisture ($H_2O$) content by electrolysis, a pumping current $I_{P1}$ flows through the oxygen pump $P_1$ and a different pumping current $I_{P2}$ flows through the oxygen pump $P_2$. The partial pressure $pH_2O$ of the moisture ($H_2O$) can be expressed as follows in gas phase equilibrium condition.

$$pH_2O = 2 \cdot kO_2 \cdot \Delta Ip \cdot \left(1 + \frac{\sqrt{pO_2}}{k(T)}\right)$$

wherein,
$pH_2O$: partial pressure of moisture in the measuring gas
$kO_2$: current constant of oxygen pump
$\Delta I_P$: $I_{P2} - I_{P1}$
$\sqrt{pO_2}$: oxygen partial pressure in the diffusion chamber In this case, as the item $\sqrt{pO_2}$ is decided by the setting voltage, the term $$\left(1 + \frac{\sqrt{pO_2}}{k(T)}\right)$$

becomes a constant. Accordingly, by measuring the two currents $I_{P2}$ and $I_{P1}$ and deriving the difference $\Delta I_P$ therebetween by processing operation and effecting calibration of the electric circuit by using gain adjustment, the moisture ($H_2O$) concentration in the measuring gas can be measured.

In the actual circuit, instead of measuring the two pumping currents $I_{P1}$ and $I_{P2}$, the voltage values are measured by the oxygen ($O_2$) converters 17 and 37 connected in parallel to the standard resistance $r_f$ respectively, and the difference between the two measured voltages is obtained by the subtracter 53. This resultant difference of the two voltages is converted by the output converter 54 into a desired display mode, for instance, into the vol % value and displayed in a desired manner.

A second embodiment shown in FIG. 4 comprises oxygen concentration cells $B_1$ and $B_2$, respectively, in addition to the sensor elements $S_1$ and $S_2$ of the above explained first embodiment for obtaining a more stable operation of the oxygen pump and the construction is modified to match with the added parts.

At the oxygen sensor element $S_1$, an oxygen concentration cell portion $B_1$ is provided underneath the oxygen pump $P_1$. The cell portion $B_1$ comprises a solid electrolyte member 20 formed of material of stabilized or partially stabilized zirconia ceramics and measuring electrodes 21 and a reference electrode 22 arranged at upper and lower sides of the solid electrolyte member 20 and formed of material such as porous platinum or the like.

Between the oxygen pump $P_1$ and the oxygen concentration cell portion $B_1$, a spacer member 23 of a predetermined thickness and formed of an insulator body is so interposed that a narrow gap flat space diffusion chamber 13 is formed to which the measuring gas is supplied under a certain predetermined diffusion resistance. At the middle portion of the diffusion chamber 13 of the oxygen pumping portion $P_1$, a gas introducing hole 24 is provided for connecting this diffusion chamber 13 to the outer space in which the measuring gas may exist. Accordingly, the measuring gas is introduced into the diffusion chamber 13 through this gas introducing hole 24 and diffused therefrom under a predetermined diffusion resistance and comes in contact with the lower pumping electrode 12 of the oxygen pumping portion $P_1$. The measuring gas also comes in contact with the measuring electrode 21 of the oxygen concentration cell portion $B_1$ at the proximity of the lower pumping electrode 12.

In the sensor element $S_2$, an oxygen concentration cell portion $B_2$ is provided over the oxygen pump $P_2$. The cell portion $B_2$ comprises a solid electrolyte member 40 formed of stabilized or partially stabilized zirconia ceramics and a reference electrode 42 and measuring electrodes 41 formed of porous platinum or the like arranged at upper and lower sides of the solid electrolyte member 40.

Between the oxygen concentration cell portion $B_2$ and the oxygen pumping portion $P_2$, a spacer member 43 of a predetermined thickness and formed of an insulator body is so interposed that a diffusion chamber 33 consisting of a narrow gap flat space is formed. At the central portion of the diffusion chamber 33 of the oxygen pumping portion $P_2$, a gas introducing hole 44 is provided for connecting this diffusion chamber 33 to the outer space in which the measuring gas may exist. The measuring gas is introduced through this gas introducing hole 44 to the diffusion chamber 33 and diffused therein with a certain diffusion resistance and comes in contact with the upper pumping electrode 31 of the oxygen pumping portion $P_2$. The measuring gas also comes in contact with the measuring electrode 41 of the oxygen concentration cell portion $B_2$ at the proximity of the upper pumping electrode 31.

Between the sensor elements $S_1$ and $S_2$, an electric insulative spacer member 46 is interposed so as to form gas passageway 45 for introducing a reference gas or reference air to the reference electrodes 22 and 42. The sensor elements $S_1$ and $S_2$ are arranged in symmetry about the central spacer member 46.

Among the electrodes, each of the upper and lower pumping electrodes 11, 31 and 12, 32 and the measuring electrodes 21 and 41 being exposed to contacts with the measuring gas, is covered by respective porous ceramic layers 61–66 formed by alumina in and the like laminated fashion. Accordingly, the measuring gas can contact with the above electrodes 11, 12 : 21, 41 : 31, 32 through the respective porous ceramic layer 61–66.

The function of the modified embodiment of the moisture measurement device will be explained by referring to the block diagram shown in FIG. 5.

The oxygen concentration cell portions $B_1$ and $B_2$ react with the measuring gas introduced into the diffusion chambers 13 and 33 through the respective gas introducing holes 24 and 44 of the oxygen pumping portions $P_1$ and $P_2$ and with the reference gas (air) and produce electromotive forces $E_1$ and $E_2$ respectively corresponding to the oxygen partial pressure ratio of the respective gases introduced. The voltages are produced between the measuring electrodes 21 and 41 and the reference electrodes 22 and 42.

The produced electromotive forces $E_1$ and $E_2$ are given by the following equation.

$$E = \frac{RT}{nF} \ell n \frac{P_A}{P_S}$$

wherein
R: gas constant
T: absolute temperature
n: ionization number
F: constant
$P_A$: Oxygen concentration of the reference gas (air)
$P_s$: oxygen concentration of the measuring gas The produced electromotive forces $E_1$ and $E_2$ appearing at terminals ⓐ and ⓑ respectively are subtracted by the setting voltages $V_1$ and $V_2$ at subtracters 71 and 72. The difference voltages therebetween i.e. ($E_1-V_1$) and ($E_2-V_2$) are applied to respective pumping current controllers 73 and 74. The pumping current controllers 73 and 74 effect proportional integrating controls and deliver predetermined control signal outputs so that the produced electromotive forces $E_1$ and $E_2$ of the oxygen pumping portions $P_1$ and $P_2$ are varied to come equal values with the Setting reference voltages $V_1$ and $V_2$, respectively. The control is effected, for instance, in the following manner.

(i) In Case of $E_1 < V_1$ or $E_2 < V_2$;

The oxygen pumping current $(I_P)$ is so controlled that the oxygen $(O_2)$ in the diffusion chamber 13 or 33 is sucked out by the oxygen pumping portion $P_1$ or $P_2$.

(ii) In case of $E_1 > V_1$ or $E_2 > V_2$;

By the regulation of the oxygen pumping Current $(I_P)$, the oxygen pumping portion $P_1$ or $P_2$ acts to introduce a more oxygen into the respective diffusion chamber 13 or 33 by the electrolysis of moisture i.e. the water content $(H_2O)$ in the measuring gas. By this regulation, the oxygen concentration in the diffusion chamber 13 or 33 is controlled to be a predetermined value.

For controlling the pumping current $(I_P)$ in the abovementioned manner, respective voltage to-current (V/I) converters 75 and 76 are provided after the pumping current $(I_P)$ controllers 73 and 74 and the output voltages of the pumping current $(I_P)$ controllers 73 and 74 are converted into the pumping currents $(I_P)$.

The oxygen concentration in the diffusion chambers 13 and 33 of the sensor elements $S_1$ and $S_2$ is maintained at a certain predetermined value. In order to obtain the desired moisture $(H_2O)$ concentration from the measured values of the two pumping currents $(I_{P1}, I_{P2})$, the outputs of respective pumping current $(I_P)$ controllers 73 and 74 are connected to a subtracter 77 through respective oxygen $(O_2)$ converters 79 and 80. In the oxygen $(O_2)$ converters 79 and 80, the output control signals derived from the pumping current $(I_P)$ controllers 73 and 74 are converted to values representing the respective oxygen concentrations and the converted $O_2$ signals are supplied to two inputs of the subtracter 77 and the difference value therebetween is derived. This difference signal corresponds to the oxygen concentration obtained by the electrolysis of the moisture $(O_2)$ content. This difference signal is converted in the succeeding output converter 78 into a value directly representing the concentration of the moisture $(H_2O)$ content in the measuring gas and displayed in the outer display device (not shown).

In the moisture measuring device having the above mentioned construction, the sensor elements are symmetrically arranged in one device so that the oxygen concentration of the reference air and that for the measuring gas including moisture can be measured simultaneously. This affords a great advantage in that no difference in the response time is required and hence the measurement error can be decreased. Also compared with the first embodiment, in which only the oxygen pumps are used, as the oxygen concentration is measured in high accuracy, the moisture measurement can be effected in high accuracy as well.

A third embodiment of the present invention will be explained by referring to FIGS. 6 and 7. As can be seen from FIG. 6, upper and lower heater portions $H_1$ and $H_2$ are provided and laminated to form an integral sensor element $S_1$ comprising an oxygen pumping portion $P_1$ and an oxygen concentration cell portion $B_1$. In this embodiment, the difference from the first and second embodiments is to measure the moisture concentration by using a single sensor element.

Figure 7B:
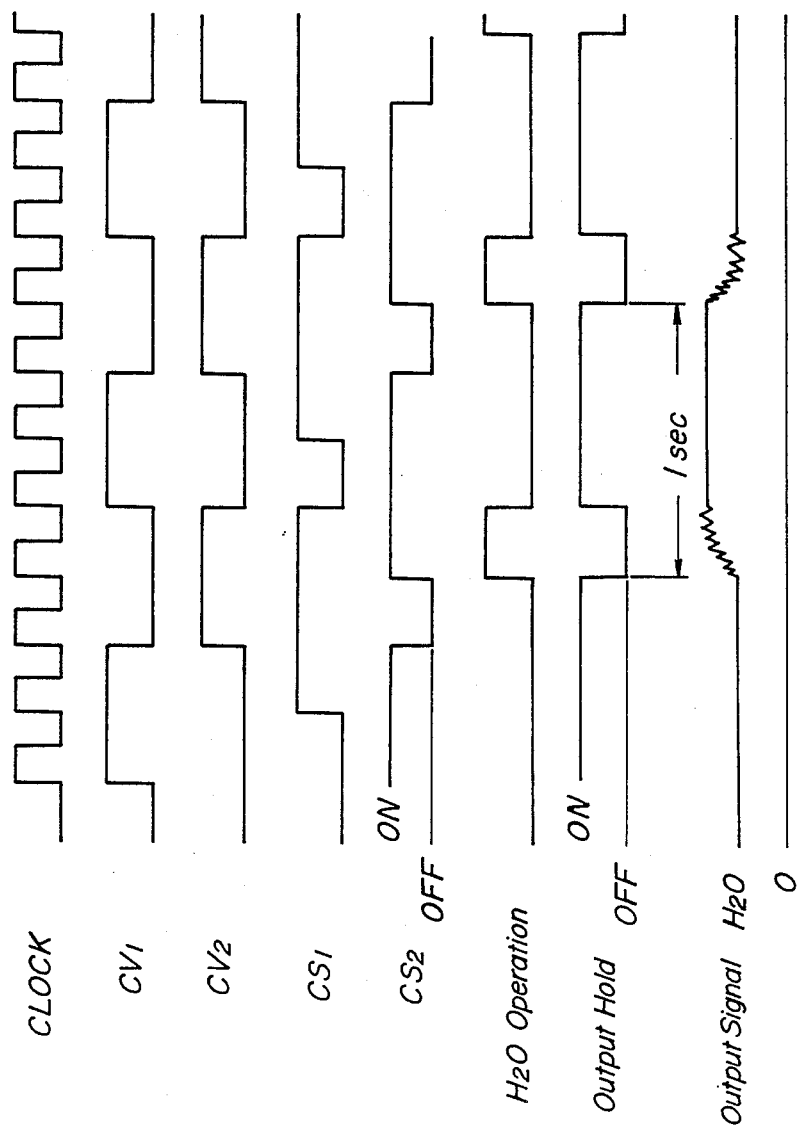

The function of this embodiment will be explained by referring to FIGS. 7A and 7B.

The electromotive force E produced in the oxygen concentration cell portion $B_1$ is subtracted by the setting voltages $V_1$ and $V_2$ alternately at a subtracter 81. The difference voltage is supplied to a pumping current $(I_P)$ controller 82 and the output control signal of this pumping current Controller 82 is applied to a voltage to current (V/I) converter 83 and to an oxygen $(O_2)$ converter 84 just as same as the second embodiment. The setting voltages $V_1$ and $V_2$ is switched by a switching element 85 at a predetermined timing supplied from a timing circuit 90.

An output signal of the oxygen $(O_2)$ converter 84 is supplied to sample-hold circuits 88 and 89 via switching elements 86 and 87, respectively. The switching elements 86 and 87 are controlled by a timing circuit (TIM) 90 in a manner that one element is in an ON condition and the other element is in an OFF condition when the setting voltage is $V_1$ and vice versa when the setting voltage is $V_2$.

The sample-hold circuits 88 and 89 hold the supplied 02 signal until the arrival of the next timing signal. The two holding signals in the circuits 88 and 89 are substracted from each other in a subtracter 91 and the output difference signal is supplied to moisture $(H_2O)$ converter 92. In the moisture $(H_2O)$ converter 92, the difference signal is added with a predetermined bias voltage to make it a value representing the moisture $(H_2O)$ concentration. The output signal is supplied to a sample-hold circuit 94 via a switching element 93 controlled by the timing circuit 90. This sample-hold circuit 94 holds the voltage representing the moistre amount and supplies this value continuously to a display device (not shown) via an output converter 95.

The timing circuit 90 is driven by a clock signal produced by a crystal oscillator or the like. This clock signal is shown in the diagram of FIG. 7B. The timing circuit 90 delivers ON signals $CV_1$ and $CV_2$ having 2 clock periods alternately to the switching element 85. Thus the switching element 85 switches between the two setting voltages $V_1$ and $V_2$ alternately. This timing circuit 90 further supplies ON signals $CS_1$ and $CS_2$ to the switching elements 86 and 87. These timing signals $CS_1$ and $CS_2$ have the ON duration for a period of 3 clock pulses. Therefore, the sample-hold circuits 88 and 89 hold the supplied signal sample for 3 clock period. During one clock periods starting from the leading edge of the ON signal $CS_2$, during which period both the signals $CS_1$ and $CS_2$ are in ON condition, the amount of moisture $(H_2O)$ is calculated by an operational process and the resultant signal is fed to the sample-hold circuit 94 through the switching element 93 which is also in ON the condition in this period. The sample-hold circuit 94 holds this output value for 3 clock periods.

According to this embodiment, the moisture concentration can be measured by a simple detecting device associated with the control and operation circuit. This embodiment has merit of having a simple construction compared with the case of using two sensor elements. Since the device is small in size, a measurement of a direct insertion system may easily be realized. Furthermore, a possible error due to the difference of respective measuring time for oxygen concentration and that additionally including oxygen content of the moisture may be negligible since it is less than the error caused by electric switching time (less than 1 sec for instance).

The moisture measuring device as explained in the foregoing is assumed to be used for measuring gas which may include moisture $(H_2O)$ but not including carbon dioxide gas. This is based on a following principle. In the oxygen pump, if the measuring gas contains such gas as $CO_2$, the following reaction occurs by (electrolysis.

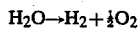

Thus the result value obtained is not directly representing the measured moisture concentration. By using this feature of the oxygen pump, the device of the present invention can be used for a case in which the measuring gas does not contains moisture but contain carbon dioxide. The device may be constructed in the same manner with the moisture measurement.

The abovementioned embodiments are concerned for the measurement of moisture in the gas which does not include carbon dioxide. However, the moisture in a combustion exhaust gas including also carbon dioxide can be measured by measurements by using two sensors as described above with reference to FIG. 4 and changing the sensor temperatures. By measuring the difference of pumping currents $\Delta I_{P1}$ (first sensor) and $\Delta I_{P2}$ (second sensor) for the electrolysis products, the concentration of $H_2O$, $CO_2$ and $O_2$ can be obtained by using the following formula.

$$\Delta I_{P1} = K_{11}CO_2 + K_{12}H_2O$$

$$\Delta I_{P2} = K_{21}CO_2 + K_{22}H_2O$$

By using the above:

$$\begin{bmatrix} CO_2 \\ H_2O \end{bmatrix} = \begin{bmatrix} K_{11} & K_{12} \\ K_{21} & K_{22} \end{bmatrix}^{-1} \begin{bmatrix} \Delta I_{P1} \\ \Delta I_{P2} \end{bmatrix}$$

The moisture measuring device according to the present invention has the particular feature in that the whole device can be made very small in size since the gas drying means such as a dehumidifier are not required and also due to the fact that the sensor element itself is of small size. Another advantage is that a short response time is realized since the time required for drying the gas is eliminated essentially and also in that the measuring error based on time shift of the measuring items is not involved in the measurement. The invention may greatly contribute in various fields of industrial application.

What is claimed is:

1. A moisture measuring device for a high temperature measurement gas, comprising:
a first substantially planar solid electrolyte sensing element consisting essentially of a solid electrolyte sensing cell, a solid electrolyte pump cell, means for defining a measurement gas diffusion chamber interposed between said cells, and a first heater member arranged adjacent said pump cell;
a second substantially planar solid electrolyte sensing element consisting essentially of a solid electrolyte sensing cell, a solid electrolyte pump cell, means for defining a measurement gas diffusion chamber interposed between said cells, and a second heater member arranged adjacent said pump cell;
means for controlling a pump current in said first sensing element by applying a first pump voltage to the pump cell of said first sensing element, said first pump voltage being of a magnitude sufficient to cause an electromotive force in the sensing cell of said first sensing element to be substantially equal to a first target voltage, said first target voltage being of a magnitude less than that required to electrolytically decompose moisture contained in said measurement gas;
means for controlling a pump current in said second sensing element by applying a second pump voltage to the pump cell of said second sensing element, said second pump voltage being of a magnitude sufficient to cause an electromotive force in the sensing cell of said second sensing element to be substantially equal to a second target voltage, said second target voltage being of a magnitude sufficient to electrolytically decompose the moisture contained in said measurement gas; and
means for measuring a difference between the pump currents flowing through the pump cells or a difference between the pump current controlling signals applied thereto, said means for measuring further including means for deriving the moisture concentration in the measurement gas from said difference between the pump currents or the pump current controlling signals.

2. A moisture measuring device according to claim 1, wherein said sensing elements are arranged symmetrically and integrally laminated via an interposed spacer member, such that reference electrodes of each sensing cell of said sensing elements are arranged adjacent each other and in communication with a common gas passageway defined by said spacer member.

3. A moisture and $CO_2$ measuring device for a high temperature measurement gas, comprising:
a first and second substantially planar solid electrolyte sensing device, each comprising two solid electrolyte sensing elements integrally laminated together via an interposed spacer member which defines a reference gas space between said elements, each of said sensing elements comprising a solid electrolyte sensing cell arranged adjacent said reference gas space, a solid electrolyte pump cell arranged adjacent said sensing cell, a measurement gas diffusion chamber interposed between said cells, and a heater member arranged adjacent said pump cell;
means for applying a first voltage to the heater members of said first sensing device to maintain said device at a first temperature;
means for controlling a pump current in a first sensing element of said first sensing device by applying a first pump voltage to a pump cell of said first sensing element, said first pump voltage being of a magnitude sufficient to cause an electromotive force in a sensing cell of said first sensing element to be substantially equal to a first target voltage, said first target voltage being of a magnitude less than that required to electrolytically decompose moisture and $CO_2$ contained in said measurement gas;
means for controlling a pump current in a second sensing element of said first sensing device by applying a second pump voltage to a pump cell of said second sensing element, said second pump voltage being of a magnitude sufficient to cause an electromotive force in a sensing cell of said second sensing element to be substantially equal to a second target voltage, said second target voltage being of a magnitude sufficient to electrolytically decompose the moisture and $CO_2$ contained in said measurement gas;

means for measuring a difference between the pump currents flowing through the pump cells of said first sensing device or a difference between the pump current controlling signals applied thereto, at said first temperature;

means for applying a second voltage to the heater members of said second sensing device to maintain said device at a second temperature;

means for controlling a pump current in a first sensing element of said second sensing device by applying a first pump voltage to a pump cell of said first sensing element, said first pump voltage being of a magnitude sufficient to cause an electromotive force in a sensing cell of said first sensing element to be substantially equal to a first target voltage, said first target voltage being of a magnitude less than that required to electrolytically decompose moisture and $CO_2$ contained in said measurement gas;

means for controlling a pump current in a second sensing element of said second sensing device by applying a second pump voltage to a pump cell of said second sensing element, said second pump voltage being of a magnitude sufficient to cause an electromotive force in a sensing cell of said second sensing element to be substantially equal to a second target voltage, said second target voltage being of a magnitude sufficient to electrolytically decompose the moisture and $CO_2$, contained in said measurement gas;

means for measuring a difference between the pump currents flowing through the pump cells of said second sensing device or a difference between the pump current controlling signals applied thereto, at said second temperature; and means for calculating the moisture and $CO_2$ concentration by using the difference of the pump currents or pump current control signals obtained from said first and second sensing devices at each of said first and second temperatures.

* * * * *